US012778297B2

(12) United States Patent
Almoaibed et al.

(10) Patent No.: US 12,778,297 B2
(45) Date of Patent: Nov. 3, 2026

(54) FIRST AID STATION

(71) Applicant: Imam Abdulrahman Bin Faisal University, Dammam (SA)

(72) Inventors: Deemah Mohammed Almoaibed, Dammam (SA); Khadijah Al Khuwaitem, Dammam (SA); Hala El-Wakeel, Dammam (SA); Amal Alkhayyal, Dammam (SA); Mai Shukri, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 6 days.

(21) Appl. No.: 18/935,152

(22) Filed: Nov. 1, 2024

(65) Prior Publication Data

US 2026/0123747 A1 May 7, 2026

(51) Int. Cl.
*A47B 95/00* (2006.01)
*A61F 17/00* (2006.01)

(52) U.S. Cl.
CPC ............ *A47B 95/008* (2013.01); *A61F 17/00* (2013.01)

(58) Field of Classification Search
CPC ......... A61F 17/00; A47B 65/15; A47B 67/02; A47B 2067/025; A47B 96/04; A47B 95/008; A47B 2200/0007
See application file for complete search history.

(56) References Cited

U.S. PATENT DOCUMENTS

| | | | | |
|---|---|---|---|---|
| 4,361,368 A * | 11/1982 | Daniels | A47B 55/00 312/405.1 |
| 6,347,831 B1 * | 2/2002 | Nye | A47B 3/14 297/118 |
| 2009/0026900 A1 * | 1/2009 | DeStefano | A45C 11/00 312/242 |
| 2011/0047696 A1 * | 3/2011 | Szekely | A47B 55/00 211/90.04 |

(Continued)

FOREIGN PATENT DOCUMENTS

| | | |
|---|---|---|
| DE | 19718274 C2 | 11/1998 |
| DE | 102020102364 A1 | 8/2021 |
| FR | 2700450 | 7/1994 |

OTHER PUBLICATIONS

"Zig Zag Storage Shelf", VE.CA Furniture, https://www.vecaetagere.com/en/shelves-design/91-20238-zig-zag-storage-shelfhtml#/91-color-white.

*Primary Examiner* — Matthew W Ing
(74) *Attorney, Agent, or Firm* — Oblon, McClelland, Maier & Neustadt, L.L.P.

(57) ABSTRACT

A first aid station including a body portion with top, upper, and lower portions formed from a single continuous sheet. The lower portion features a serpentine structure forming repeating compartments, each with surfaces created by horizontal and vertical runs of the sheet. A rectangular structure on the upper portion, combined with the top portion, forms an enclosed cabinet. The serpentine structure creates shelves from pairs of horizontal runs, extending perpendicularly from vertical runs. Removable incident boxes, each with a (Continued)

lid connected by rotating pins, are housed in the compartments. The integrated construction of the first aid station enhances durability and ease of manufacturing, while its modular nature facilitates maintenance and restocking, potentially improving emergency response in various settings.

21 Claims, 9 Drawing Sheets

(56) References Cited

U.S. PATENT DOCUMENTS

| | | | | |
|---|---|---|---|---|
| 2011/0062834 | A1* | 3/2011 | Ball | A62C 35/20 312/215 |
| 2013/0180202 | A1* | 7/2013 | Woods | A47B 95/008 52/710 |
| 2014/0034648 | A1* | 2/2014 | Peterson | B25H 3/022 220/507 |
| 2018/0366220 | A1* | 12/2018 | Liao | G07C 9/21 |
| 2022/0042324 | A1 | 2/2022 | De La O, Jr. et al. | |

* cited by examiner

FIRST AID STATION

BACKGROUND

Technical Field

The present disclosure relates to the field of first aid equipment and storage systems. More specifically, the present disclosure relates to wall-mounted first aid stations designed for use in primary schools and other work environments where quick access to organized first aid supplies is required.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

First aid stations are necessary commodities in various settings, including schools, workplaces, and public spaces. These stations provide immediate access to medical supplies and equipment necessary for addressing minor injuries and emergency situations. In educational environments, particularly primary schools, there is a need for efficient and well-organized first aid stations due to the frequency of minor accidents and injuries among young students. However, the existing designs and implementations of first aid stations in primary schools face several challenges. These include inadequate organization of supplies, difficulty in quickly locating specific items during emergencies, and lack of clear instructions for the use of first aid materials. Additionally, traditional first aid kits may not be easily accessible to staff members who are not trained medical professionals but are often the first responders in school-based incidents. These issues can lead to delays in providing timely and effective first aid, potentially exacerbating injuries or causing unnecessary distress to students.

Some solutions have been proposed to address these issues, such as portable first aid kits, wall-mounted cabinets, and labeled storage containers. Portable first aid kits offer mobility but often lack organization and may not be consistently located in the same place. Wall-mounted cabinets provide a fixed location for supplies but may not offer efficient categorization or easy access to specific items. Labeled storage containers can improve organization but may not address the need for clear instructions or quick retrieval of supplies in stressful situations. Many existing systems lack the ability to efficiently categorize supplies based on specific types of injuries, which can lead to confusion and delays in administering first aid. Furthermore, these solutions may not adequately address the psychological barriers that untrained staff members face when confronted with the need to provide first aid, such as a lack of confidence or a lack of knowledge regarding how to handle the emergency situation. Therefore, while these solutions provide some advances, they still fall short in providing a comprehensive system that combines accessibility, organization, and clear guidance for use in high-stress situations.

DE19718274C2 describes a household medicine chest designed to be mounted on the inner side of a wardrobe or cabinet wall. This device features one or more shelves to carry medicines and preparations, with a guide for a carrier and shelf that can be positioned as required and moved out of the interior of the cupboard. The design includes side parts made as stamped and bent parts from a sheet metal blank, with a housing installed between upper shelves. While this solution provides some improvements in terms of storage and accessibility, it is primarily designed for household use and does not specifically address the unique needs and challenges of a school environment, particularly in terms of organization, quick access, and user guidance for first aid situations.

Accordingly, it is one object of the present disclosure to provide an improved first aid station that addresses these limitations, particularly in primary school environments. The present disclosure addresses the aforementioned needs with a first aid station for mounting on a vertical surface, which provide efficient organization, clear instructions, and a design that enables non-medical staff to confidently and effectively administer first aid when necessary. The first aid station of the present disclosure combines the benefits of fixed location, efficient categorization, clear guidance, and ease of access, while also considering the specific needs and frequency of incidents in a primary school setting.

SUMMARY

In an exemplary embodiment, a first aid station for mounting on a vertical surface is described. The first aid station comprises a body portion having a top portion, an upper portion, and a lower portion. Herein, the top portion, the upper portion, and the lower portion are formed of a single continuous sheet. The upper portion is flat and configured to mount the first aid station vertically to the vertical surface. The lower portion has a serpentine structure forming three repeating compartments. Each compartment has a bottom surface formed by a first horizontal run of the single continuous sheet, a front surface formed by a first vertical run of the single continuous sheet, a top surface formed by a second horizontal run of the single continuous sheet, and a back surface formed by a second vertical run of the single continuous sheet. The first aid station further comprises at least one rectangular structure mounted on the upper portion of the single continuous sheet comprising a back, left, right, and bottom surface forming a walled compartment. The top portion of the single continuous sheet overlays the walled compartment to form an enclosed cabinet. Herein, the repeating compartments of the serpentine structure of the lower portion form a plurality of shelves. Each pair of horizontal runs forms a single shelf. The first horizontal and second horizontal runs extend perpendicular from the first vertical run. The first vertical run facing away from the vertical surface. The second vertical run extends perpendicularly from the first second horizontal run. The second vertical run faces towards the vertical surface. The first and second horizontal runs extend perpendicularly from a vertical plane, running parallel to a horizontal plane. The first aid station further comprises three incident boxes each comprising a lid, an outer structure, and an inner compartment. The lid has at least two rotating pins connecting the lid to the outer structure. Each incident box is removably disposed in one compartment of the repeating compartments of the serpentine structure.

In some embodiments, the single continuous sheet is formed of a material selected from the group consisting of a stainless steel, an acrylic, an aluminum, an acrylonitrile butadiene styrene (ABS) plastic, a pine wood, and a high-density polyethylene (HDPE).

In some embodiments, the single continuous sheet is formed of aluminum.

In some embodiments, each front surface has a height of 40 to 70 mm.

In some embodiments, the upper portion has a height of 250 to 350 mm.

In some embodiments, the first aid station has a height of at least 700 mm.

In some embodiments, the first aid station has a length of at least 200 mm.

In some embodiments, the first aid station has a width of at least 250 mm.

In some embodiments, each of the incident boxes comprise at least one selected from the group consisting of a high-density polyethylene (HDPE), a low-density polyethylene (LDPE), a polypropylene (PP), a polycarbonate (PC), and a polyvinyl chloride (PVC).

In some embodiments, each of the incident boxes comprise HDPE.

In some embodiments, the top portion has a height of at least 90 mm.

In some embodiments, both the top surface and the bottom surface have a length of at least 200 mm and a width of at least 250 mm.

In some embodiments, the rectangular structure has a height of at least 250 mm, a length of at least 100 mm, and a width of at least 110 mm.

In some embodiments, a section of the body portion between the rectangular structure and the lower portion has a height of at least 90 mm.

In some embodiments, the lid of each incident box further comprises a set of unique instructions to assist a user during a medical incident.

In some embodiments, each incident box has a height of at least 40 mm.

In some embodiments, each incident box has a length of at least 200 mm.

In some embodiments, each incident box has a width of at least 250 mm.

In some embodiments, the body portion further comprises a plurality of hooks configured to mount the first aid station to the vertical surface.

In some embodiments, each back surface has a height of 5 to 25 mm.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
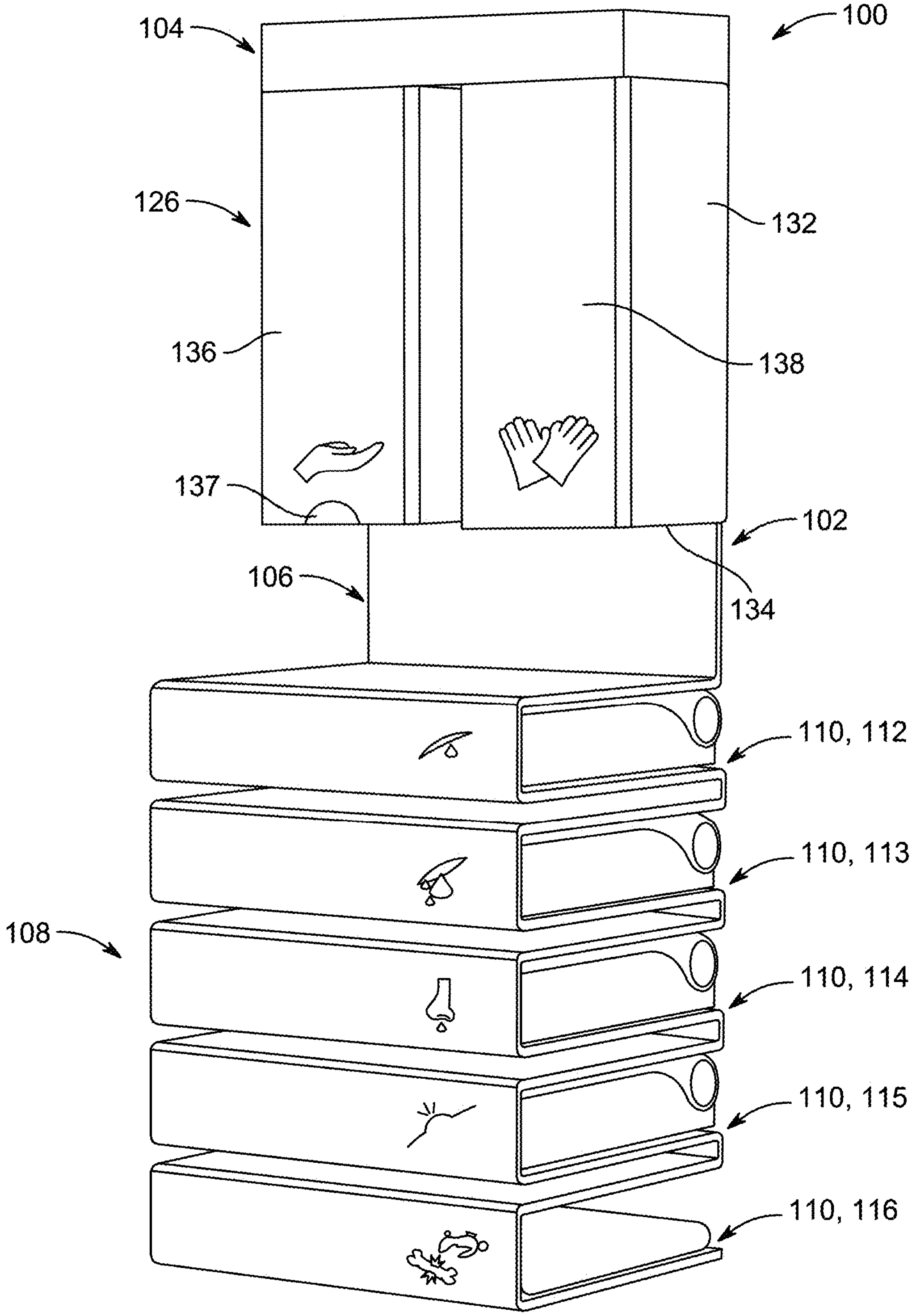
FIG. 1 is an exemplary perspective diagram of a first aid station for mounting on a vertical surface, according to certain embodiments.

In the drawings, like reference numerals designate identical or corresponding parts throughout the several views. Further, as used herein, the words “a,” “an” and the like generally carry a meaning of “one or more,” unless stated otherwise.

Furthermore, the terms “approximately,” “approximate,” “about,” and similar terms generally refer to ranges that include the identified value within a margin of 20%, 10%, or preferably 5%, and any values therebetween.

Aspects of this disclosure are directed to a first aid station that addresses critical needs in various environments where quick and efficient access to medical supplies is required. The first aid station of the present disclosure is designed to streamline the process of accessing and using first aid supplies, potentially reducing response times in critical situations. The configuration of the first aid station allows for improved visibility, accessibility, and organization of supplies, making it particularly valuable in settings such as schools, workplaces, public facilities, and other high-traffic areas where accidents or medical emergencies may occur. The first aid station of the present disclosure distinguishes itself from known devices through its integrated approach to storage, access, and guidance. While traditional first aid solutions often focus solely on supply storage, the present first aid station incorporates features that actively assist users in selecting appropriate supplies and administering first aid correctly. This approach enhances the effectiveness of first aid provision and also enables individuals with varying levels of medical training to respond confidently in emergency situations.

Figure 2:
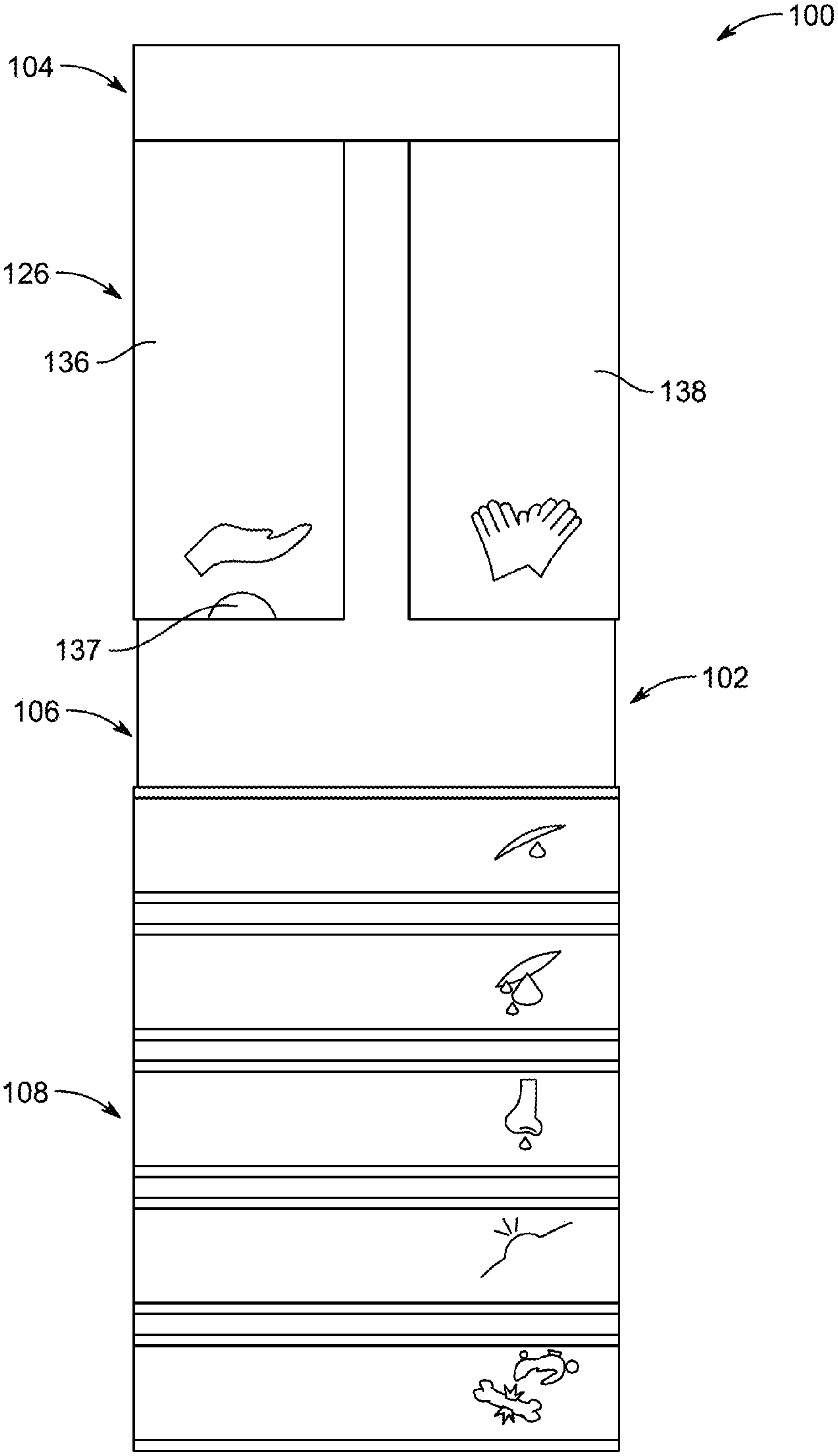
FIG. 2 is an exemplary front planar diagram of the first aid station, according to certain embodiments.
Figure 3:
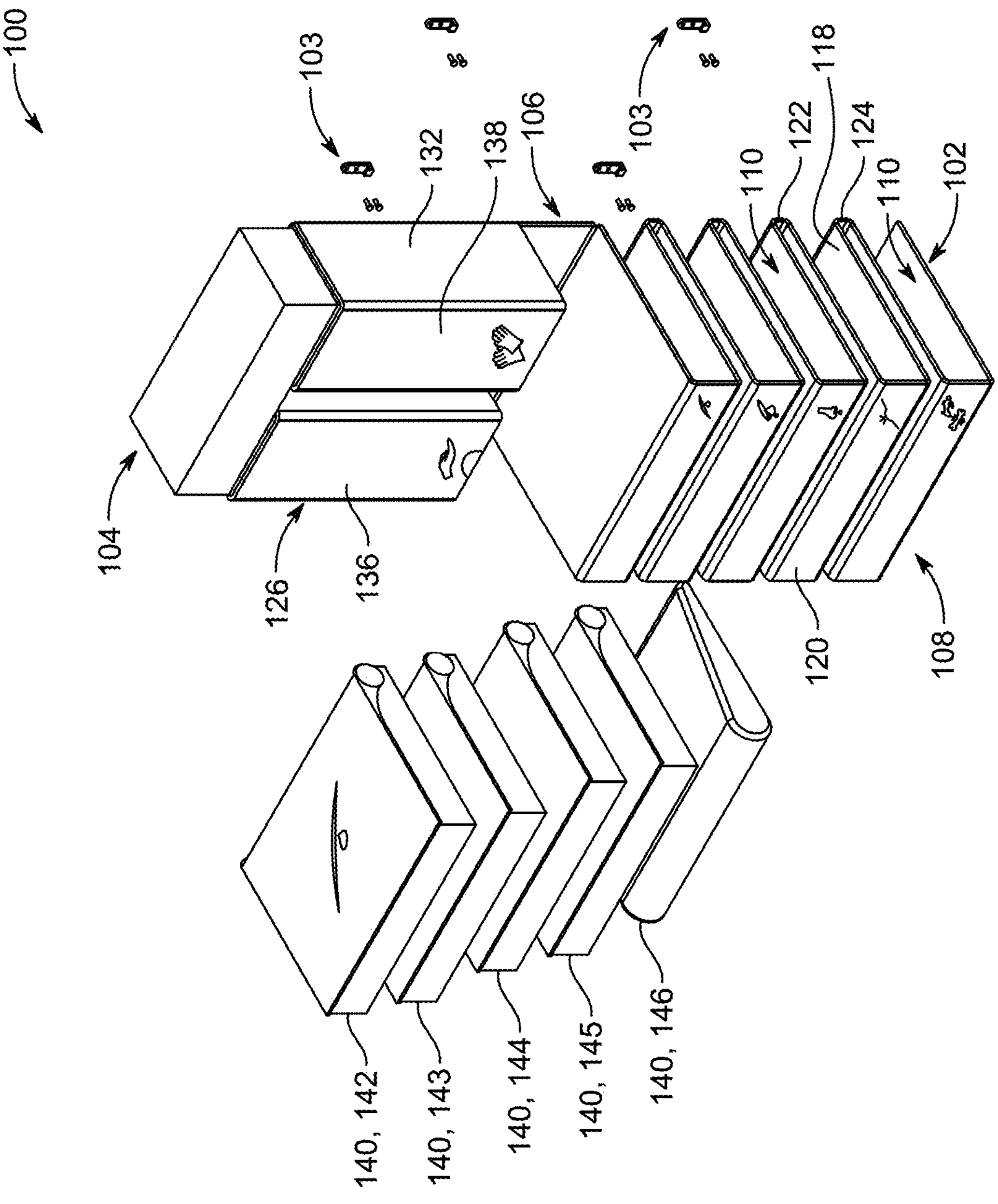
FIG. 3 is an exemplary exploded perspective diagram of the first aid station, according to certain embodiments.

Referring to FIGS. 1-3 in combination, illustrated is a first aid station 100 as per embodiments of the present disclosure. The first aid station 100 is configured for mounting on a vertical surface, such as a wall or the like, providing a secure and easily accessible location for first aid supplies in various environments. The first aid station 100 incorporates multiple storage compartments arranged in a visually intuitive and ergonomic manner, facilitating quick access to necessary supplies during emergencies. The first aid station 100 features a combination of fixed and removable components, allowing for both secure storage and portable access to supplies as needed. The layout of the first aid station 100 is designed to maximize visibility and organization of supplies, with designated areas for different types of first aid materials and equipment. The first aid station 100 of the present disclosure is suitable for a wide range of settings such as schools, offices, public spaces, and industrial environments.

In one embodiment, the first aid station 100 includes a body portion 102 having a top portion 104, an upper portion 106, and a lower portion 108. The top portion 104, the upper portion 106, and the lower portion 108 are formed of a single continuous sheet. The continuous sheet forming the body portion 102 allows for a smooth transition between the top portion 104, the upper portion 106, and the lower portion 108. The smooth transitions between portions minimize areas where dust or contaminants could accumulate, facilitating easy cleaning and maintenance of the first aid station 100. This continuous sheet also provides structural integrity to the first aid station 100 and simplifies the manufacturing process. Additionally, the use of a single continuous sheet for the body portion 102 reduces the number of joints or seams in the structure, potentially increasing the durability and longevity of the first aid station 100.

The overall dimensions of the first aid station 100, including all portions of the body portion 102, are designed to provide a balance between storage capacity and space efficiency. This balance ensures that the first aid station 100 can accommodate a wide range of necessary supplies while remaining compact enough for practical installation in various environments. In one embodiment, the first aid station 100 has a height of at least 700 mm, preferably at least 705 mm, preferably at least 710 mm, preferably at least 715 mm, preferably at least 720 mm, preferably at least 725 mm, preferably at least 730 mm, preferably at least 735 mm, most preferably at least 740 mm. This minimum height allows for a vertical arrangement of supplies, maximizing storage capacity within a limited wall area. Further, the first aid station 100 has a length of at least 200 mm, preferably at least 205 mm, preferably at least 210 mm, preferably at least 215 mm, preferably at least 220 mm, preferably at least 225 mm, most preferably at least 230 mm. This length provides adequate horizontal space for storing first aid supplies of various sizes and shapes. Further, the first aid station 100 has a width of at least 250 mm, preferably at least 252 mm, preferably at least 254 mm, preferably at least 256 mm, preferably at least 258 mm, preferably at least 260 mm, preferably at least 262 mm, preferably at least 264 mm, preferably at least 266 mm, preferably at least 268 mm, most preferably at least 270 mm. This width allows for sufficient depth, enabling storage of bulkier items while still maintaining a relatively slim profile when mounted on the vertical surface. The given dimensions maintain a compact and efficient form factor, allowing the first aid station 100 to be installed in various settings.

In present embodiments, the single continuous sheet is formed of a material selected from the group consisting of a stainless steel, an acrylic, an aluminum, an acrylonitrile butadiene styrene (ABS) plastic, a pine wood, and a high-density polyethylene (HDPE). Stainless steel offers excellent durability and resistance to corrosion, making it suitable for environments where the first aid station 100 may be exposed to moisture or chemicals. Acrylic provides a lightweight and visually appealing option, with good impact resistance and clarity. ABS plastic combines the strength and rigidity of acrylonitrile and styrene polymers with the toughness of polybutadiene rubber, resulting in a material that is both strong and lightweight. Pine wood offers a natural aesthetic and can be treated for durability, potentially suiting environments where a more organic look is desired. HDPE provides excellent chemical resistance and impact strength, making it suitable for a wide range of environments. In a preferred embodiment, the single continuous sheet is formed of aluminum. Aluminum offers a high strength-to-weight ratio, making it sturdy enough to support the structure and contents of the first aid station 100 while keeping the overall weight manageable for mounting on the vertical surface. The selection of aluminum or any of the other materials from the group allows for customization of the first aid station 100 to suit specific environmental needs, regulatory requirements, and aesthetic preferences, while maintaining the functional design and structural integrity of the first aid station 100.

As shown in FIG. 3, the body portion 102 of the first aid station 100 includes a plurality of hooks 103 configured to mount the first aid station 100 to the vertical surface. These hooks 103 are designed to provide secure and stable attachment of the first aid station 100 to walls or other vertical surfaces in various environments. The hooks 103 are positioned on the body portion 102 to distribute the weight of the first aid station 100 evenly across the mounting surface. Each hook 103 is designed to work in conjunction with fasteners. These fasteners may include screws, bolts, or other appropriate hardware suitable for the specific mounting surface (e.g., drywall, concrete, or wooden studs). The number and placement of hooks 103 on the body portion 102 are determined based on the overall dimensions and weight distribution of the first aid station 100. The hooks 103 are typically constructed of a durable material, such as a metal, to provide long-lasting support and resist wear over time. This mounting arrangement ensures a secure attachment of the first aid station 100 to vertical surfaces while facilitating easy installation and potential repositioning if needed.

In the first aid station 100, the top portion 104 of the body portion 102 serves as the uppermost section of the first aid station 100. The top portion 104 is formed from a part of the single continuous sheet that also forms the upper portion 106 and the lower portion 108. In some embodiments, the top portion 104 has a height of at least 90 mm, preferably at least 91 mm, preferably at least 92 mm, preferably at least 93 mm, preferably at least 94 mm, preferably at least 95 mm, preferably at least 96 mm, most preferably at least 97 mm. This height provides sufficient space for additional storage or functional elements within the upper section of the first aid station 100. The top portion 104 may overlay a rectangular structure to form an enclosed cabinet, as will be discussed in more detail later.

The upper portion 106 is flat and is configured to mount the first aid station 100 vertically to the vertical surface. This flat configuration of the upper portion 106 is configured to ensure stable and secure mounting of the first aid station 100 on walls or other vertical surfaces in various environments such as schools, workplaces, or public spaces. The flat nature of the upper portion 106 provides a large surface area for contact with the vertical surface, enhancing the stability of the mounted first aid station 100. This configuration helps distribute the weight of the first aid station 100 evenly across the mounting area, reducing stress on any single point of attachment. In some embodiments, the upper portion 106 has a height of 250 to 350 mm, providing sufficient space for securely mounting hardware and ensuring a strong connection to the vertical surface. The upper portion 106 has a height of 250 to 350 mm, preferably 252 to 348 mm, preferably 254 to 346 mm, preferably 256 to 344 mm, preferably 258 to 342 mm, preferably 260 to 340 mm, preferably 262 to 338 mm, preferably 264 to 336 mm, preferably 266 to 334 mm, preferably 268 to 334 mm, preferably 270 to 334 mm, preferably 270 to 332 mm, preferably 270 to 330 mm, preferably 270 to 328 mm, preferably 270 to 326 mm, preferably 270 to 324 mm, preferably 270 to 322 mm, preferably 270 to 320 mm, preferably 270 to 318 mm, preferably 270 to 316 mm, preferably 270 to 314 mm, preferably 270 to 312 mm, preferably 270 to 310 mm, preferably 270 to 308 mm, preferably 270 to 306 mm, preferably 270 to 304 mm, preferably 270 to 302 mm, preferably 270 to 300 mm, preferably 270 to 298 mm, preferably 270 to 296 mm, preferably 270 to 294 mm, preferably 270 to 292 mm, preferably 270 to 290 mm, preferably 270 to 288 mm, preferably 270 to 286 mm, preferably 270 to 284 mm, preferably 270 to 282 mm, preferably 270 to 280 mm, preferably 270 to 278 mm, preferably 270 to 276 mm, preferably 270 to 274 mm, preferably 270 to 272 mm, most preferably 270 mm. This height also allows for the incorporation of additional features in the upper section of the first aid station 100, such as the rectangular structure that forms the enclosed cabinet when combined with the top portion 104.

Figure 4:
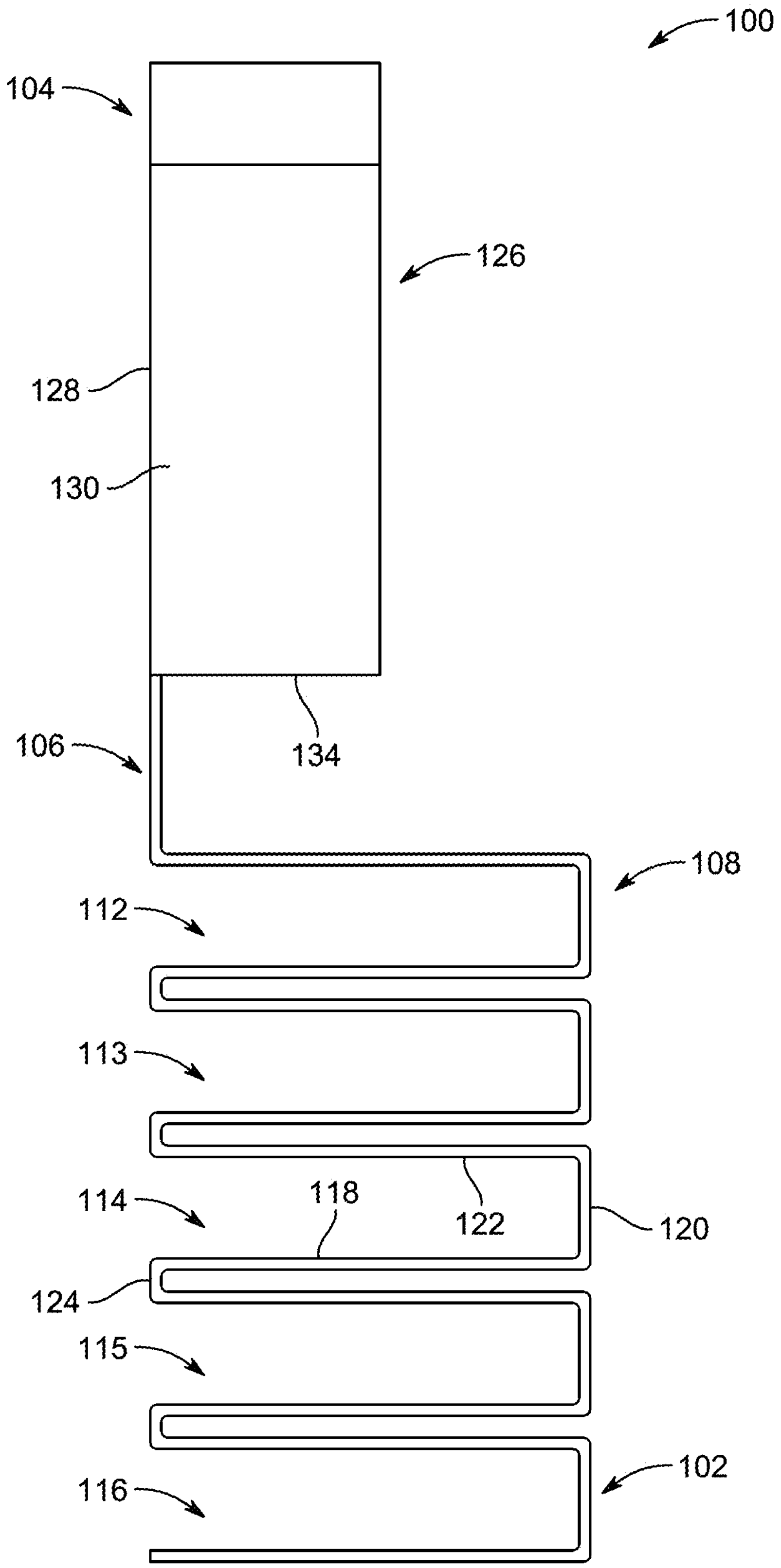
FIG. 4 is an exemplary side planar diagram of the first aid station with incident boxes removed therefrom, according to certain embodiments.

The lower portion 108 of the first aid station 100 has a serpentine structure forming three repeating compartments (commonly represented by 110). In the illustrated embodiments, the lower portion 108 of the first aid station 100 is shown to include five such compartments, including a first compartment 112, a second compartment 113, a third compartment 114, a fourth compartment 115, and a fifth compartment 116 (as represented in FIG. 4). The serpentine structure is formed from the single continuous sheet that comprises the entire body portion 102 of the first aid station 100. As better shown in FIGS. 3 and 4, each compartment 110 has a bottom surface (generally and commonly represented by 118) formed by a first horizontal run of the single continuous sheet. The bottom surface 118 provides a stable base for storing first aid supplies or incident boxes within each compartment. The first horizontal run extends perpendicularly from the vertical plane of the first aid station 100, creating a shelf-like structure. A front surface 120 of each compartment 110 is formed by a first vertical run of the single continuous sheet. The front surface 120 extends upwards from a front edge of the bottom surface 118, creating the forward boundary of each compartment. In some embodiments, each front surface 120 has a height of 40 to 70 mm, providing sufficient space for storing common first aid supplies while maintaining a compact profile. Each front surface 120 has a height of 40 to 70 mm, preferably 42 to 68 mm, preferably 44 to 66 mm, preferably 46 to 64 mm, preferably 48 to 62 mm, preferably 50 to 60 mm, preferably 52 to 58 mm, preferably 54 to 56 mm, most preferably 55 mm. A top surface 122 of each compartment 110 is formed by a second horizontal run of the single continuous sheet. The top surface 122 extends backwards from an upper edge of the front surface 120, running parallel to the bottom surface 118. The top surface 122 serves as both a cover for the current compartment and a bottom surface for the compartment above it in the serpentine structure. A back surface 124 of each compartment 110 is formed by a second vertical run of the single continuous sheet. The back surface 124 extends downwards from a rear edge of the bottom surface 118, completing the enclosure of each compartment. In some embodiments, each back surface 124 has a height of 5 to 25 mm, providing sufficient gaps between two consecutive compartments 110. Each back surface 124 has a height of 5 to 25 mm, preferably 6 to 24 mm, preferably 7 to 23 mm, preferably 8 to 22 mm, preferably 9 to 21 mm, preferably 10 to 20 mm, preferably 11 to 19 mm, preferably 12 to 18 mm, preferably 13 to 17 mm, preferably 14 to 16 mm, most preferably 15 mm. As may be seen, the back surface 124 faces towards the vertical surface on which the first aid station 100 is mounted.

The serpentine (castle line) structure created by the alternating horizontal and vertical runs forms the series of open-faced compartments 110 that are easily accessible from sides of the first aid station 100. This configuration allows for efficient organization of first aid supplies and facilitates quick retrieval of needed items in emergency situations. The dimensions of each compartment 110 are configured to accommodate standard first aid supplies or custom-designed incident boxes. In some embodiments, both the top surface 122 and the bottom surface 118 of each compartment have a length of at least 200 mm and a width of at least 250 mm. In some embodiments, both the top surface 122 and the bottom surface 118 of each compartment have a length of at least 200 mm, preferably at least 205 mm, preferably at least 210 mm, preferably at least 215 mm, preferably at least 220 mm, most preferably 225 mm. In some embodiments, both the top surface 122 and the bottom surface 118 of each compartment have a width of at least 250 mm, preferably at least 255 mm, preferably at least 260 mm, preferably at least 265 mm, preferably at least 270 mm, most preferably at least 275 mm. These dimensions provide sufficient space for storing a range of first aid supplies within each compartment 110. The continuous nature of the sheet forming the serpentine structure ensures structural integrity and seamless transitions between the compartments 110.

In one embodiment, the repeating compartments 110 of the serpentine structure of the lower portion 108 form a plurality of shelves. This shelving system provides organized storage space for first aid supplies and/or incident boxes. Each pair of horizontal runs in the serpentine structure forms a single shelf. Specifically, the first horizontal run forming the bottom surface 118 of one compartment and the second horizontal run forming the top surface 122 of the compartment, collectively create a single shelf unit. This configuration allows for efficient use of the vertical space within the first aid station 100. The first horizontal run and the second horizontal run extend perpendicular from the first vertical run to define volume of the shelf. This perpendicular configuration creates a right-angled structure that provides stability to the shelves and defines the depth of each compartment 110. The first vertical run, which forms the front surface 120 of each compartment, faces away from the vertical surface on which the first aid station 100 is mounted. This orientation helps to contain items within each compartment 110. The second vertical run, which forms the back surface 124 of each compartment, extends perpendicularly from the second horizontal run. The second vertical run faces toward the vertical surface on which the first aid station 100 is mounted. The orientation of the back surface 124 provides additional stability to the shelf structure. The first horizontal run and the second horizontal run extend perpendicularly from a vertical plane, running parallel to a horizontal plane. Herein, the vertical plane and the horizontal plane are defined relative to the mounting orientation of the first aid station 100 on the vertical surface. The vertical plane is parallel to the vertical surface on which the first aid station 100 is mounted, while the horizontal plane is perpendicular to the vertical surface and parallel to the ground. This parallel configuration of the horizontal runs ensures that each shelf is level, providing a stable surface for storing first aid supplies or incident boxes. The perpendicular relationship between the horizontal and vertical runs creates a structure capable of supporting the weight of stored items. This configuration creates a stable and efficient shelving system within the serpentine structure. The alternating pattern of horizontal and vertical runs forms a series of open-faced compartments 110 that are easily accessible from the sides of the first aid station 100. Each shelf is designed to securely hold first aid supplies or removable incident boxes, allowing for organized storage and quick retrieval of items when needed.

In one or more embodiments, both the top surface 118 and the bottom surface 122 have a length of at least 200 mm and a width of at least 250 mm. In one or more embodiments, each bottom surface 122 of each compartment has a projection 156 rising from the bottom surface 122 and extending the entire width of the bottom surface 122 from a first open end to a second open end of the compartment, wherein each projection 156 has a height of from 2 to 10 mm and a width of from 1 to 5 mm and is configured to elevate an incident box present in the compartment such that a first portion of the incident box is elevated above the bottom surface 122 of the compartment and a second portion of the incident box rests directly on the bottom surface 122.

In one or more embodiments, each bottom surface 122 of each compartment has a projection 158 rising from the bottom surface 122 and extending a part of the width of the bottom surface 122, wherein each projection 158 has a height of from 2 to 10 mm and a width of from 1 to 5 mm and is configured to elevate an incident box present in the compartment such that a first portion of the incident box is elevated above the bottom surface 122 of the compartment and a second portion of the incident box rests directly on the bottom surface 122.

The first aid station 100 also comprises at least one rectangular structure 126 mounted on the upper portion 106 of the single continuous sheet. The rectangular structure 126 is designed to integrate with the overall design of the first aid station 100, providing a dedicated area for storing items that may require restricted access or are less frequently used. The rectangular structure 126 includes a back, left, right, and bottom surface, forming a walled compartment. Specifically, as shown, the rectangular structure 126 includes a back surface 128 (generally represented in FIG. 4), a left-side surface 130, a right-side surface 132, and a bottom surface 134. These surfaces 128, 130, 132, and 134 create a three-dimensional space within the upper section of the first aid station 100. Herein, the back surface 128 is positioned against the upper portion 106 of the single continuous sheet, ensuring stability and proper alignment of the rectangular structure 126 within the first aid station 100. Further, the left-side surface 130 and the right-side surface 132 extend perpendicularly from the back surface 128, defining the lateral boundaries of the walled compartment. These side surfaces 130, 132 provide structural support and help to contain items stored within the rectangular structure 126. The bottom surface 134 connects the lower edges of the back surface 128, the left-side surface 130, and the right-side surface 132, forming the base of the walled compartment. To complete the enclosed structure, the top portion 104 of the single continuous sheet overlays the walled compartment. This configuration forms an enclosed cabinet, providing a secure and protected storage space within the first aid station 100. The integration of the top portion 104 with the rectangular structure 126 provides a seamless and aesthetically pleasing design while maximizing the functional storage capacity of the first aid station 100.

Such enclosed cabinet formed by the combination of the rectangular structure 126 and the top portion 104 serves multiple purposes within the first aid station 100. In one embodiment, the rectangular structure 126 provides a secure storage area for sensitive items, such as certain medications or specialized equipment, that should not be readily accessible to all users. Additionally, the enclosed cabinet can house less frequently used supplies, keeping them organized and protected while ensuring that the more commonly used items in the lower compartments remain easily accessible. The dimensions of the rectangular structure 126 are carefully considered to provide ample storage space while maintaining the overall compact profile of the first aid station 100. In some embodiments, the rectangular structure 126 has a height of at least 250 mm, a length of at least 100 mm, and a width of at least 110 mm. In some embodiments, the rectangular structure 126 has a height of at least 250 mm, preferably at least 255 mm, preferably at least 260 mm, preferably at least 265 mm, preferably at least 270 mm. In some embodiments, the rectangular structure 126 has a length of at least 100 mm, preferably at least 105 mm, preferably at least 110 mm, preferably at least 115 mm, most preferably at least 120 mm. In some embodiments, the rectangular structure 126 has a width of at least 110 mm, preferably at least 111 mm, preferably at least 112 mm, preferably at least 113 mm, preferably at least 114 mm, most preferably at least 115 mm. These dimensions create a sizeable-enclosed space for storing additional first aid supplies or equipment that may require restricted access. Further, a section of the body portion 102 between the rectangular structure 126 and the lower portion 108 has a height of at least 90 mm, preferably 91 mm, preferably at least 92 mm, preferably at least 93 mm, preferably at least 94 mm, preferably at least 95 mm, preferably at least 96 mm, most preferably at least 97 mm, providing sufficient space to access the rectangular structure 126 from bottom (if needed). The materials used for the rectangular structure 126 may be selected to complement the single continuous sheet of the body portion 102, such as aluminum, stainless steel, or high-impact plastics, depending on the specific requirements of the installation environment. The choice of material ensures durability, ease of cleaning, and compatibility with the overall design aesthetic of the first aid station 100.

In some embodiments, the rectangular structure 126 of the first aid station 100 is divided into two compartments, a first compartment 136 and a second compartment 138. This division allows for specialized storage and dispensing of different types of first aid supplies, enhancing the functionality and organization of the first aid station 100. In particular, the first compartment 136 of the rectangular structure 126 may be implemented for dispensing sanitizer. The first compartment 136 is configured to accommodate a sanitizer container, such as a gallon-sized bottle, which can be refilled as needed. At the bottom of the first compartment 136, a spray mechanism 137 (e.g., an automatic, touchless spray dispenser) is mounted. The spray mechanism 137 is configured to connect with the sanitizer container when it is placed inside the compartment 136. This feature ensures a secure connection between the sanitizer container and the spray mechanism 137, facilitating easy filling and efficient dispensing of sanitizer. The second compartment 138 of the rectangular structure 126 is designed for dispensing gloves. The second compartment 138 may have a hole at the bottom (not shown in the figures) through which gloves can be pulled. The design of this hole allows for easy access to the gloves while keeping the remaining gloves protected within the compartment 138. This configuration enables users to quickly retrieve gloves when needed, which is particularly important in emergency situations where time is of the essence. Both the first compartment 136 and the second compartment 138 may have logos printed or embossed on their surfaces for reference (as shown). These logos provide clear visual indicators of the contents of each compartment, allowing users to quickly identify and locate the sanitizer and/or gloves, as required. Thus, the rectangular structure 126, with its division into these specialized compartments 136, 138, enhances the overall functionality of the first aid station 100.

Moreover, as illustrated, the first aid station 100 further comprises three incident boxes (commonly represented by 140). Each incident box 140 is configured to be removably disposed in one compartment of the repeating compartments 110 of the serpentine structure in the lower portion 108 of the first aid station 100. This removable configuration allows for easy access, replacement, and restocking of supplies as needed. In the illustrated embodiments, the first aid station 100 is shown to incorporate four incident boxes, a first incident box 142, a second incident box 143, a third incident box 144, and a fourth incident box 145. These incident boxes are designed to fit into their respective compartments in the lower portion 108 of the first aid station 100. Specifically, the first incident box 142 is removably disposed in the first compartment 112, the second incident box 143 in the second compartment 113, the third incident box 144 in the third compartment 114, and the fourth incident box 145 in the fourth compartment 115. In addition to the incident boxes, the first aid station 100 further comprises a supportive tool 146, which is removably disposed in the fifth compartment 116 of the lower portion 108. The supportive tool 146 is designed to assist in specific first aid scenarios and complements the supplies contained in the incident boxes 140, in the implementation of the first aid station 100.

Figure 5:
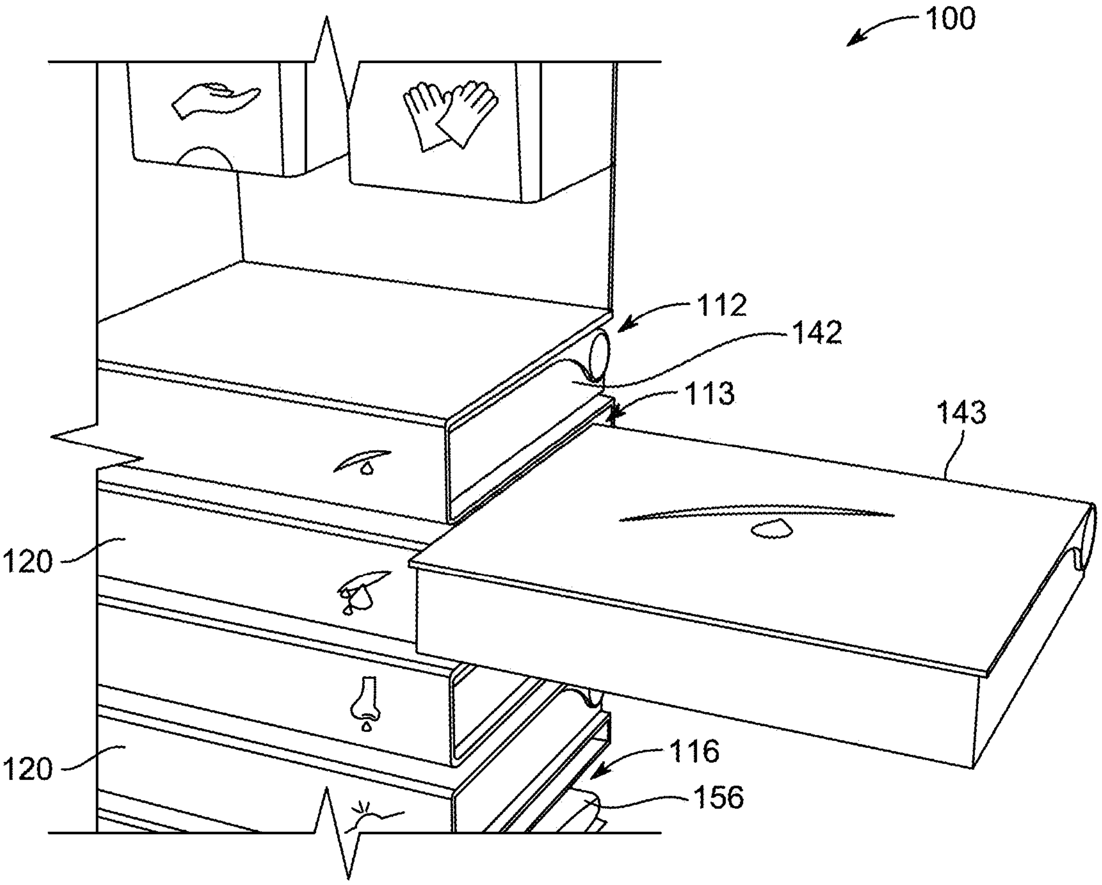
FIG. 5 is an exemplary partial diagram of the first aid station illustrating removal of one of the incident boxes therefrom, according to certain embodiments.

FIG. 5 provides an exemplary partial diagram of the first aid station 100 illustrating removal of one of the incident boxes 143 from its respective compartment 113. The incident box 143 is designed to slide out of its compartment 113 in a horizontal direction. This sliding mechanism allows for smooth and efficient removal of the incident boxes 140 from easily accessible sides of the first aid station 100. The sliding action is facilitated by the design of both the incident boxes 140 and the compartments 110. Each of the incident boxes 140 are shaped to fit snugly within the respective compartment 110, while still allowing for easy movement. The ability to slide out the incident box 143 demonstrates the ease with which all the incident boxes 142, 143, 144, 145 can be accessed and removed from the first aid station 100. It may be appreciated that the supportive tool 146 may also be slide out from the respective compartment 116. This design feature significantly enhances the usability of the first aid station 100 in emergency situations, where quick access to specific supplies is needed. The sliding mechanism allows for rapid retrieval of the incident box/supportive tool 146, which can then be taken directly to the site of the emergency, if necessary. Furthermore, this removable design facilitates efficient restocking and maintenance of the first aid station 100. Empty or depleted incident boxes can be quickly and easily slid out and replaced with fully stocked ones, ensuring that the first aid station 100 is always ready for use.

Figure 6:
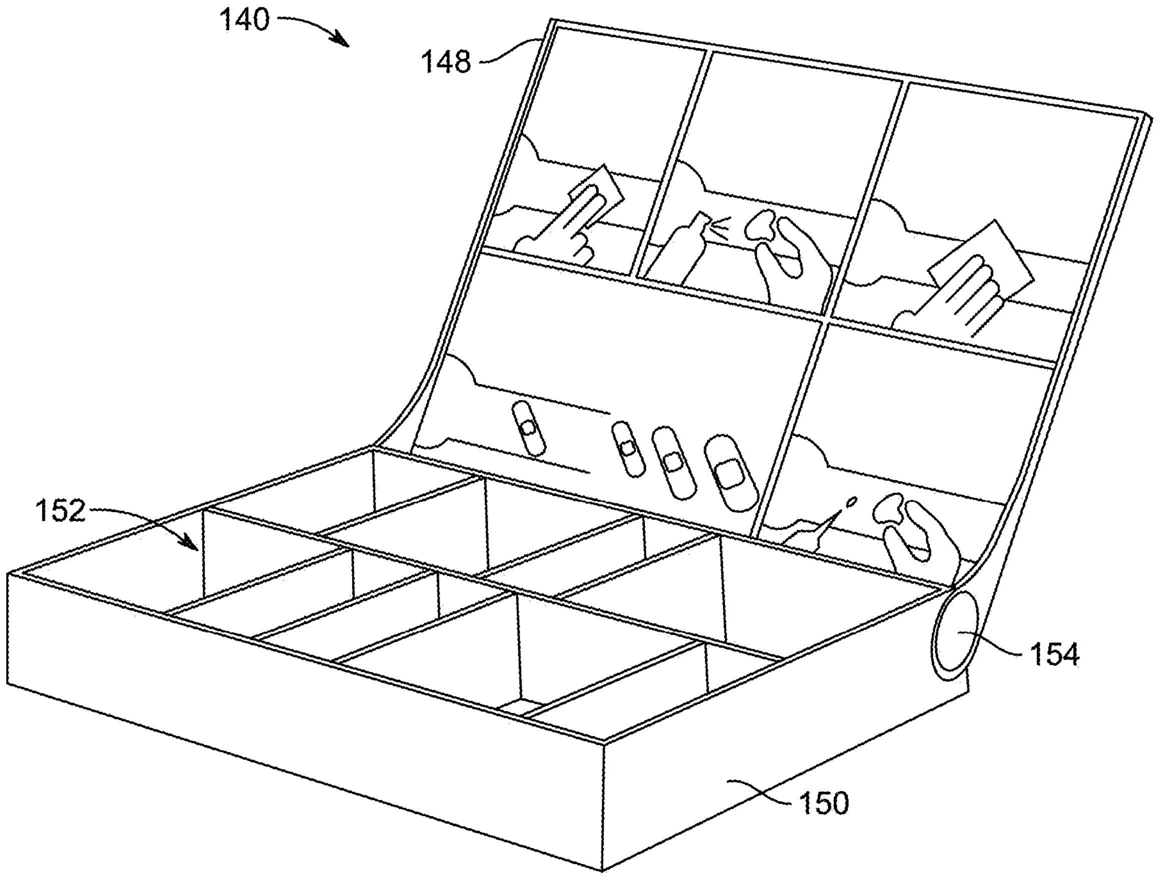
FIG. 6 is an exemplary perspective diagram of one of the incident boxes with its lid in open position, according to certain embodiments.

Referring to FIG. 6, an exemplary perspective diagram of one of the incident boxes 140 is illustrated in an open position. In one embodiment, each incident box 140 comprises a lid 148, an outer structure 150, and an inner compartment 152. The lid 148 of each incident box 140 is connected to the outer structure 150 by at least two rotating pins 154. These rotating pins 154 allow the lid 148 to be opened and closed smoothly, providing easy access to the supplies contained within the inner compartment 152 while ensuring that the lid 148 remains securely attached to the outer structure 150. The outer structure 150 of each incident box 140 forms the main body of the box, providing structural integrity and protection for the supplies contained within. The outer structure 150 is configured to fit snugly into the compartments 110 of the serpentine structure, ensuring that the incident boxes 140 remain secure when stored in the first aid station 100, yet can be easily removed when needed. The inner compartment 152 of each incident box 140 is designed to store the first aid supplies and items. As shown, the inner compartment 152 may be divided or organized to accommodate various types of supplies/items, depending on the specific purpose of each incident box 140. For example, one incident box may be dedicated for treating cuts and scrapes and may contain supplies related thereto, while another incident box may be dedicated to burns or eye injuries and may contain materials for addressing those issues.

In the first aid station 100, each incident box 140 is configured with specific minimum dimensions to ensure adequate storage capacity for a range of first aid supplies while maintaining compatibility with the compartments in the lower portion 108 of the first aid station 100. Each incident box 140 has a height of at least 40 mm, preferably at least 41 mm, preferably at least 42 mm, preferably at least 43 mm, preferably at least 44 mm, preferably at least 45 mm, most preferably at least 46 mm. This height requirement ensures that the incident boxes 140 can accommodate a variety of first aid supplies, including items that may have some vertical dimension, such as rolls of bandages, small bottles, and the like. Each incident box 140 has a length of at least 200 mm, preferably at least 205 mm, preferably at least 210 mm, preferably at least 215 mm, most preferably at least 220 mm. This length dimension allows the incident boxes 140 to store longer items such as arm slings, larger bandage rolls, or multiple smaller items arranged in an organized manner. Each incident box 140 has a width of at least 250 mm, preferably at least 255 mm, preferably at least 260 mm, preferably at least 265 mm, most preferably at least 270 mm. This width provides a substantial area for the incident boxes 140 to allow for efficient organization of supplies.

In present embodiments, each of the incident boxes 140 includes at least one selected from the group consisting of a high-density polyethylene (HDPE), a low-density polyethylene (LDPE), a polypropylene (PP), a polycarbonate (PC), and a polyvinyl chloride (PVC). HDPE is known for its high strength-to-density ratio, making it both sturdy and lightweight. HDPE also offers excellent resistance to many solvents and chemicals, which is beneficial for storing various first aid supplies. LDPE provides flexibility and toughness, with good resistance to impacts and chemicals. PP offers a good balance of strength and flexibility, with excellent fatigue resistance. PP is also highly resistant to many chemical solvents, acids, and bases, which can be beneficial for storing various types of first aid supplies. PC is known for its high impact strength and excellent transparency, which could be useful if visual identification of the box contents is desired without opening the lid 148. PVC provides good chemical resistance and durability. In present embodiments, preferably, each of the incident boxes 140 is composed of HDPE. This preference for HDPE is based on several factors that make it particularly suitable for the application in the first aid station 100, such as a high strength-to-density ratio, which ensures that the incident boxes 140 are robust enough to protect the first aid supplies they contain, while remaining light enough for easy removal and transport in emergency situations.

Figure 7A:
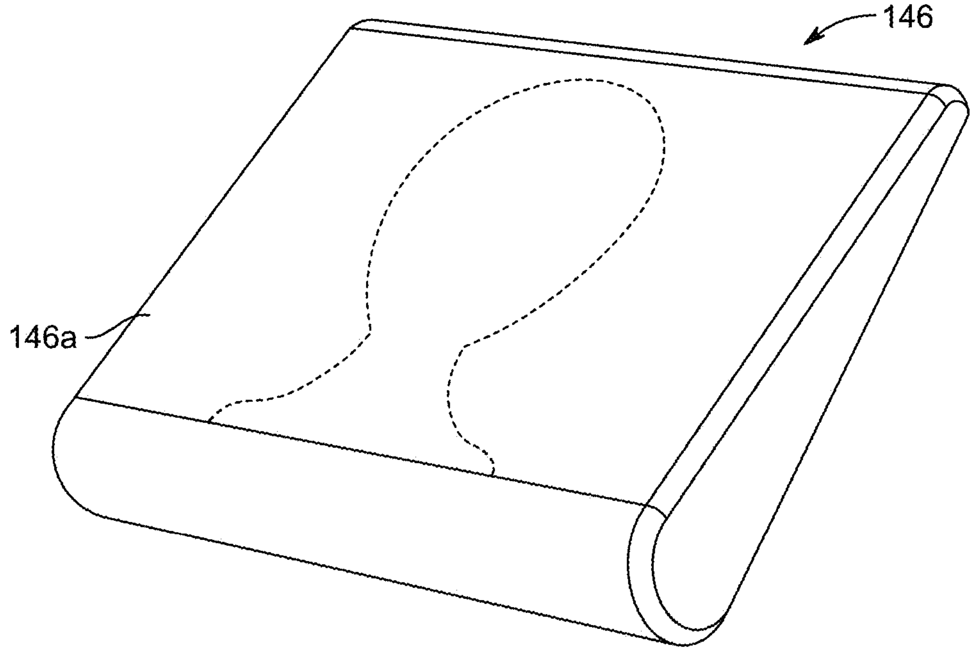
FIG. 7A is an exemplary perspective diagram of a supportive tool of the first aid station showing a first side thereof, according to certain embodiments.
Figure 7B:
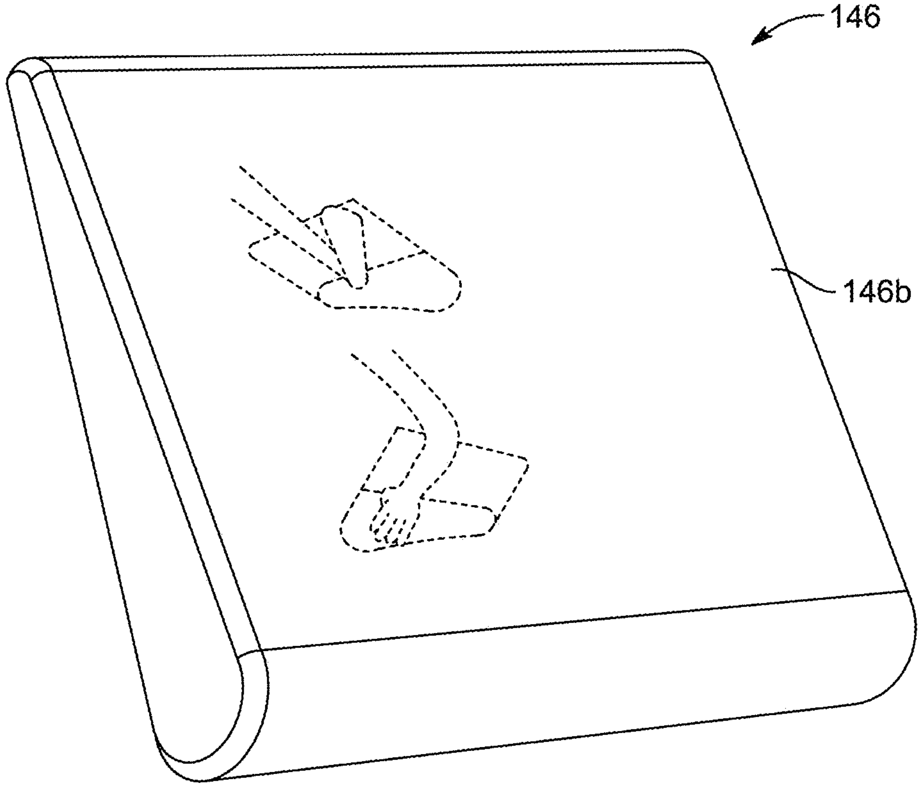
FIG. 7B is an exemplary perspective diagram of the supportive tool showing a second side thereof, according to certain embodiments.
Figure 8:
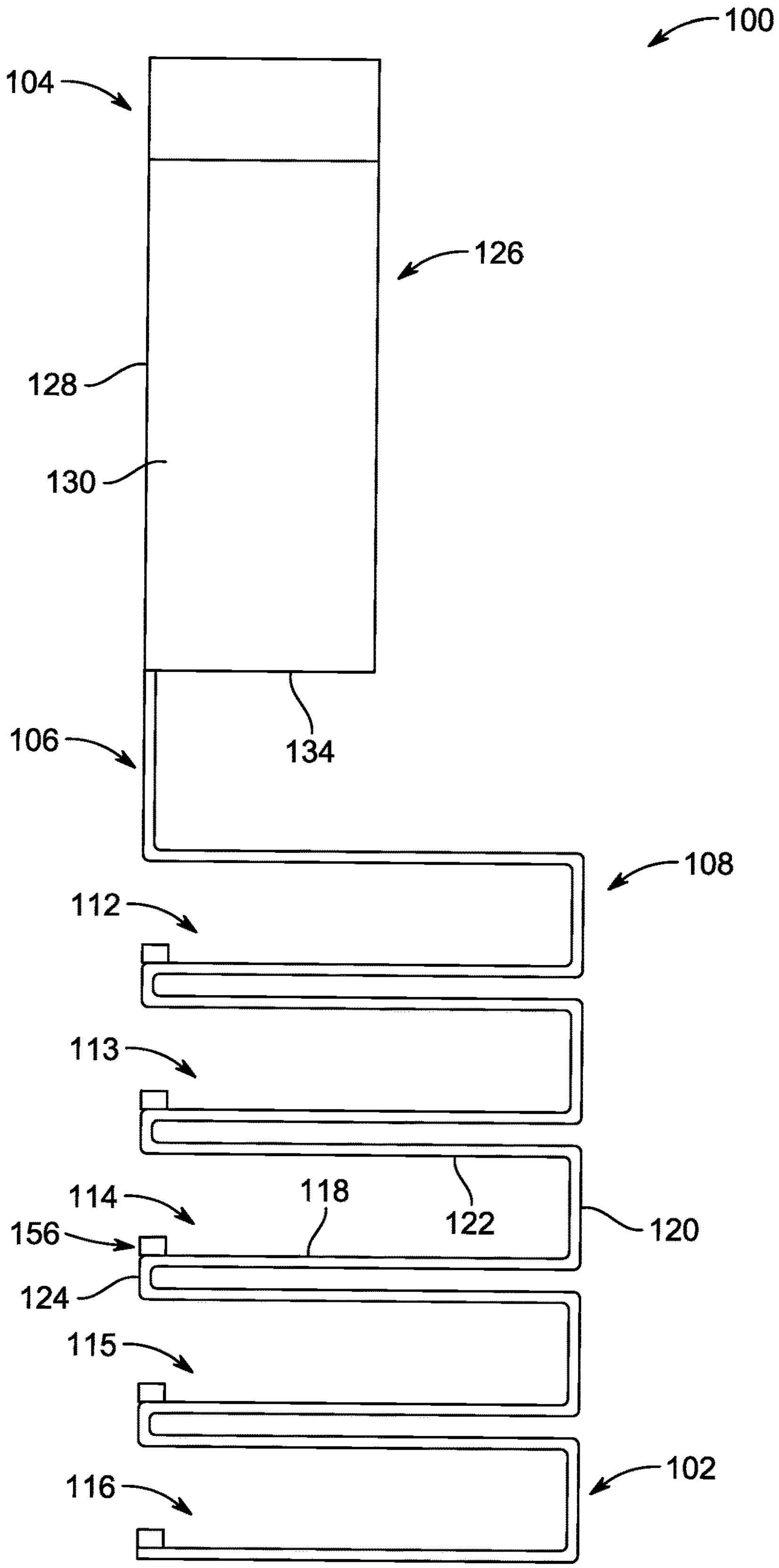
FIG. 8 is an exemplary side planar diagram of the first aid station with incident boxes removed therefrom showing an added projection, according to certain embodiments.
Figure 9:
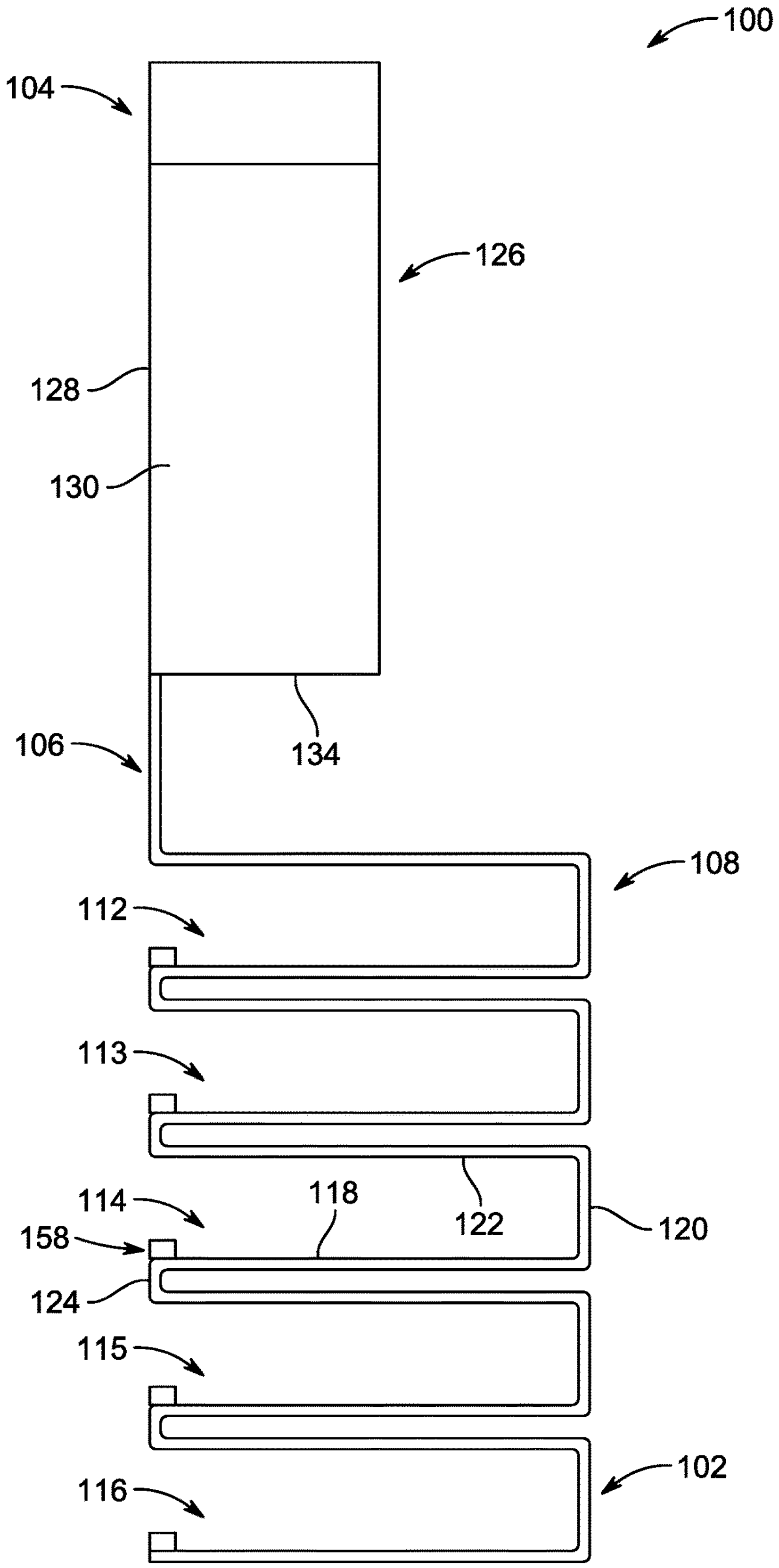
FIG. 9 is an exemplary side planar diagram of the first aid station with incident boxes removed therefrom showing an added projection, according to certain embodiments.

FIGS. 7A and 7B illustrate exemplary perspective diagrams of the supportive tool 146 of the first aid station 100. FIG. 7A shows a first side 146*a* of the supportive tool 146, while FIG. 7B shows a second side 146*b*. The supportive tool 146 has a two-sided design, allowing it to serve dual purposes. Each side is specifically configured to address either seizures or fractures, with clear labeling and instructions for each use case. The first side 146*a*, as shown in FIG. 7A, is configured for use during seizures. The first side 146*a* may provide a thick side designed to help keep the airway open when positioned under the patient's head. The first side 146*a* may feature an illustration in a shape of a head to guide the user to properly place head of the patient. The first side 146*a* may also feature labeling indicating "For Seizure" to ensure proper usage in emergency situations. The second side 146*b*, as shown in FIG. 7B, is configured for fracture support. The second side 146*b* may feature clear labeling indicating "For Fractures" to guide proper usage, along with a warning to only support the injured part and not move it. The second side 146*b* may also feature illustrations demonstrating the correct positioning for various types of fractures, providing visual guidance for users. The dual-purpose nature of the supportive tool 146 allows it to address a wider range of medical emergencies, enhancing the versatility of the first aid station 100.

For purposes of the present disclosure, the supportive tool 146 may be constructed using Polyurethane Laminate (PUL) fabric. This fabric choice provides durability, flexibility, and ease of cleaning, which are important characteristics for a medical support tool. The interior of the supportive tool 146 may be filled with thick foam and/or a cotton filling, creating a firm yet comfortable support structure. The supportive tool 146 is designed to fit within the fifth compartment 116 of the lower portion 108 of the first aid station 100. The supportive tool 146 has a unique shape with one thick side that gradually tapers, specifically designed to support the head during seizure incidents. In general, the supportive tool 146 is designed to be of compact shape, which allows for easy storage while still providing effective support in emergency situations.

In some embodiments, as better shown in FIG. 6, the lid 148 of each incident box 140 further comprises a set of unique instructions to assist a user during a medical incident. These instructions are designed to provide clear, step-by-step guidance for addressing specific types of injuries or medical situations, enhancing the usability of the first aid station 100 even for users with limited first aid training. The instructions on the lid 148 are typically presented in a clear, easy-to-read format. In some embodiments, the instructions may be organized in steps, such as numbered steps, with each step accompanied by text and/or pictorial representations. For example, the instructions may comprise steps for applying pressure, cleaning a wound, and bandaging. This combination of textual and visual information helps to ensure that the instructions can be quickly understood and followed in emergency situations. In a present embodiment, the lid 148 is configured to stop at 60 degrees to align with sight level. This ergonomic design feature ensures that when an incident box 140 is opened, the instructions on the inside of the lid 148 are presented at an optimal viewing angle. This configuration enhances readability and usability, allowing users to easily reference the instructions while accessing the supplies within the incident box 140.

Furthermore, in some embodiments, as shown in FIG. 4, a top surface of the lid 148 of each incident box 140 features icons or logos for quick identification. These icons are designed to be easily recognizable and indicative of the specific type of medical supplies or the nature of injuries the box is intended to address. These icons may include simplified representations of common injuries such as a nose with a droplet for nosebleeds, a zigzag line for fractures, or a bandage for wounds. Correspondingly, the front surface 120 of each respective compartment 110 in the lower portion 108 of the first aid station 100 displays the same icon as the one on the lid 148 of the incident box 140 it is designed to hold. Further, as may be seen, the front surface 120 of the compartment 116 designated for the supportive tool 146 also features an icon for easy identification. This icon is typically distinctive from those used for the incident boxes 140, clearly indicating the specialized nature of the supportive tool 146. In an example, the icon for the supportive tool 146 may combine elements representing both fractures and seizures, reflecting its dual-purpose nature. This labeling system, with feature of matching icons, allows users to easily identify incident box 140/supportive tool 146 for sliding out in an emergency situation, while also providing a visual confirmation, once it has been removed, that the correct incident box 140/supportive tool 146 has been selected. This labeling system enhances the speed and accuracy of supply retrieval in emergency situations. This labeling system also helps ensure that each incident box 140/supportive tool 146 is returned to its correct compartment 110 after use, maintaining the organized structure of the first aid station 100 and facilitating quick access in future emergencies.

In various embodiments, the first aid station 100 incorporates a child-resistant design, with secure locking mechanisms on the removable incident boxes 140 to prevent unauthorized access by children. The incident boxes 140 of the first aid station 100 feature internal divisions labeled with tool names to ensure correct and consistent refilling of supplies. The first aid station 100 comprises a barcode system on the instruction lids 148 of the incident boxes 140, providing access to additional detailed information when scanned. These barcodes may be scanned by a mobile device to open an application or an internet site with the additional detailed information. This barcode scanning may be performed by methods known in the art such as by QR codes and the like. The body portion 102 of the first aid station 100 may be manufactured using a rotational molding process for the incident boxes 140, allowing for uniform wall thickness and integrated internal divisions. The shelves of the lower portion 108 are fabricated from aluminum sheets using CNC machining for precise cutting and hole placement, followed by a bending process to achieve the desired shape.

The first aid station 100 of the present disclosure comprises a unique serpentine structure in the lower portion 108, forming multiple compartments 110 for storing the removable incident boxes 140, combined with the use of the supportive tool 146, is configured to be implemented for first aid equipment organization and accessibility. The serpentine structure of the lower portion 108 provides efficient space utilization while ensuring easy access to supplies. The removable incident boxes 140, each dedicated to specific types of injuries, allow for quick retrieval and potential transport of supplies to the site of an emergency. The enclosed cabinet formed by the rectangular structure 126 and the top portion 104 offers secure storage for sensitive or less frequently used items. The use of the single continuous sheet for the body portion 102 enhances structural integrity and simplifies manufacturing. The inclusion of clear labeling, icons, and instructions on both the incident boxes 140 and their corresponding compartments 110 facilitates rapid identification and proper use of supplies, even by users with minimal first aid training. The first aid station 100 addresses limitations in existing systems through its comprehensive and user-centric design. The discussed features collectively result in the first aid station 100 that is more efficient, user-friendly, and versatile than existing solutions, potentially improving response times and outcomes in emergency situations.

Numerous modifications and variations of the present disclosure are possible in light of the above teachings. It is therefore to be understood that within the scope of the appended claims, the invention may be practiced otherwise than as specifically described herein.

The invention claimed is:

1. A first aid station for mounting on a vertical surface, comprising:

- a body portion having a top portion, an upper portion, and a lower portion, wherein the top portion, the upper portion, and the lower portion are formed of a single continuous sheet,
- wherein the upper portion is flat and is configured to mount the first aid station vertically to the vertical surface;
- wherein the lower portion has a serpentine structure forming three repeating compartments, each compartment having a bottom surface formed by a first horizontal run of the single continuous sheet, a front surface formed by a first vertical run of the single continuous sheet, a top surface formed by a second horizontal run of the single continuous sheet, and a back surface formed by a second vertical run of the single continuous sheet;
- at least one rectangular structure mounted on the upper portion of the single continuous sheet comprising a back, left, right, and bottom surface forming a walled compartment, the top portion of the single continuous sheet overlaying the walled compartment to form an enclosed cabinet; and
- wherein the repeating compartments of the serpentine structure of the lower portion form a plurality of shelves, wherein each pair of horizontal runs forms a single shelf, the first horizontal and second horizontal runs extending perpendicular from the first vertical run, the first vertical run facing away from the vertical surface,
- wherein the second vertical run extends perpendicularly from the second horizontal run, the second vertical run facing towards the vertical surface, and the first and second horizontal runs extending perpendicularly from a vertical plane, running parallel to a horizontal plane,
- wherein the first horizontal and second horizontal runs are only connected by the first vertical run,
- wherein each single shelf comprises a first open end and a second open end, and
- three incident boxes each comprising a lid, an outer structure, and an inner compartment, the lid having at least two rotating pins connecting the lid to the outer structure, wherein each incident box is removably disposed in one compartment of the repeating compartments of the serpentine structure.

2. The first aid station of claim 1, wherein the single continuous sheet is formed of a material selected from the group consisting of a stainless steel, an acrylic, an aluminum, an acrylonitrile butadiene styrene (ABS) plastic, a pine wood, and a high-density polyethylene (HDPE).

3. The first aid station of claim 1, wherein the single continuous sheet is formed of aluminum.

4. The first aid station of claim 1, wherein each front surface has a height of 40 to 70 mm.

5. The first aid station of claim 1, wherein the upper portion has a height of 250 to 350 mm.

6. The first aid station of claim 1, having a height of at least 700 mm.

7. The first aid station of claim 1, having a length of at least 200 mm.

8. The first aid station of claim 1, having a width of at least 250 mm.

9. The first aid station of claim 1, wherein each of the incident boxes comprise at least one selected from the group consisting of a high-density polyethylene (HDPE), a low-density polyethylene (LDPE), a polypropylene (PP), a polycarbonate (PC), and a polyvinyl chloride (PVC).

10. The first aid station of claim 1, wherein each of the incident boxes comprise HDPE.

11. The first aid station of claim 1, wherein the top portion has a height of at least 90 mm.

12. The first aid station of claim 1, wherein both the top surface and the bottom surface have a length of at least 200 mm and a width of at least 250 mm, and

- wherein each bottom surface of each compartment has a projection rising from the bottom surface and extending the entire width of the bottom surface from a first open end to a second open end of the compartment, wherein each projection has a height of from 2 to 10 mm and a width of from 1 to 5 mm and is configured to elevate an incident box present in the compartment such that a first portion of the incident box is elevated above the bottom surface of the compartment and a second portion of the incident box rests directly on the bottom surface.

13. The first aid station of claim 1, wherein the rectangular structure has a height of at least 250 mm, a length of at least 100 mm, and a width of at least 110 mm.

14. The first aid station of claim 1, wherein both the top surface and the bottom surface have a length of at least 200 mm and a width of at least 250 mm, and

- wherein each bottom surface of each compartment has a projection rising from the bottom surface and extending a part of the width of the bottom surface, wherein each projection has a height of from 2 to 10 mm and a width of from 1 to 5 mm and is configured to elevate an incident box present in the compartment such that a first portion of the incident box is elevated above the bottom surface of the compartment and a second portion of the incident box rests directly on the bottom surface.

15. The first aid station of claim 1, wherein the lid of each incident box further comprises a set of unique instructions to assist a user during a medical incident.

16. The first aid station of claim 1, wherein each incident box has a height of at least 40 mm.

17. The first aid station of claim 1, wherein each incident box has a length of at least 200 mm.

18. The first aid station of claim 1, wherein each incident box has a width of at least 250 mm.

19. The first aid station of claim 1, wherein the body portion further comprises a plurality of hooks configured to mount the first aid station to the vertical surface.

20. The first aid station of claim 1, wherein each back surface has a height of 5 to 25 mm.

21. The first aid station of claim 1, further comprising a supportive tool.

* * * * *